US007256408B2

(12) United States Patent
Nakamura

(10) Patent No.: US 7,256,408 B2
(45) Date of Patent: Aug. 14, 2007

(54) GAS SUPPLY UNIT, GAS SUPPLY METHOD AND EXPOSURE SYSTEM

(75) Inventor: Yoshiharu Nakamura, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/282,621

(22) Filed: Nov. 21, 2005

(65) Prior Publication Data

US 2006/0071184 A1 Apr. 6, 2006

Related U.S. Application Data

(62) Division of application No. 10/446,328, filed on May 27, 2003, now Pat. No. 6,987,276.

(30) Foreign Application Priority Data

May 27, 2002 (JP) ............................ 2002/153008

(51) Int. Cl.
*A61N 5/06* (2006.01)

(52) U.S. Cl. ....................... 250/504 R; 355/30; 355/35

(58) Field of Classification Search ............ 250/504 R; 355/30
See application file for complete search history.

(56) References Cited

U.S. PATENT DOCUMENTS

| | | | | |
|---|---|---|---|---|
| 4,540,466 | A * | 9/1985 | Nishizawa | 438/708 |
| 6,633,364 | B2 * | 10/2003 | Hayashi | 355/53 |
| 6,987,276 | B2 * | 1/2006 | Nakamura | 250/492.2 |
| 7,145,629 | B2 * | 12/2006 | Nakano | 355/30 |

* cited by examiner

*Primary Examiner*—David A. Vanore
(74) *Attorney, Agent, or Firm*—Morgan & Finnegan, LLP

(57) ABSTRACT

A gas supply unit supplies gas to a certain space via a channel, and includes a first switch mechanism located in the channel for selectively changing the channel of the gas.

15 Claims, 10 Drawing Sheets

PRIOR ART

GAS SUPPLY UNIT, GAS SUPPLY METHOD AND EXPOSURE SYSTEM

This application is a divisional application of U.S. application Ser. No. 10/446,328, filed May 27, 2003, now U.S. Pat. No. 6,987,276 entitled "Gas Supply Unit, Gas Supply Method And Exposure System". Aforementioned, U.S. application Ser. No. 10/446,328, filed May 27, 2003, is incorporated by reference herein in its entirety.

This application claims the right of priority under 35 U.S.C. § 119 based on Japanese Patent Application No. 2002-153008, filed on May 27, 2002, which is hereby incorporated by reference herein in its entirety as if fully set forth herein.

BACKGROUND OF THE INVENTION

The present invention relates generally to gas supply units and methods for supplying inert gas to an exposure apparatus, and exposure systems using the same. In particular, the present invention is suitable for a gas supply unit, as well as to an exposure system, for supplying inert gas to an exposure light path of a projection exposure apparatus that uses far UV light and an excimer laser beam as a light source.

Along with recent demands on smaller and lower profile electronic devices, fine semiconductor devices to be mounted onto these electronic devices have been increasingly demanded. The conventional printing or photolithography for fabricating semiconductor devices has used a projection exposure apparatus.

In general, a projection exposure apparatus includes an illumination optical system that uses light emitted from a light source to illuminate a mask, and a projection optical system arranged between the mask and an object to be exposed. For a uniform illumination area, the illumination optical system introduces light from a light source into a light integrator, such as a fly-eye lens composed of multiple rod lenses, and uses a light exit plane of the light integrator as a secondary light source plane to Koehler-illuminate the mask plane through a condenser lens.

The minimum critical dimension to be transferred by the projection exposure apparatus (resolution) is proportionate to a wavelength of light used for exposure, and inversely proportionate to the numerical aperture of the projection optical system. The shorter the wavelength is, the better the resolution is.

Accordingly, the light source in recent years has been in transition from an ultra-high pressure mercury lamp (g-line with a wavelength of approximately 436 nm) and i-line with a wavelength of approximately 365 nm) to KrF excimer laser (with a wavelength of approximately 248 nm) and ArF excimer laser (with a wavelength of approximately 193 nm). Practical use of $F_2$ excimer laser (with a wavelength of 157 nm) has been promoted.

It is known that i-line or other exposure light with a shorter wavelength results in a photochemical reaction between the impurity in the air and oxygen ($O_2$) due to its short wavelength, which generates products to adhere to and opaque an optical element, such as a lens and a mirror in an optical system.

The products typically include ammonium sulfate ($(NH_4)_2SO_4$), for example, which is produced by sulfuric acid ($SO_2$) that reacts with oxygen in the air or oxidizes when it absorbs light energy and gets excited. Ammonium sulfate is whitish and opaques an optical element, such as a lens and mirror, when it adheres to a surface of the optical element. Ammonium sulfate disperses and absorbs the exposure light, and lowers the transmittance of an optical system, thus greatly reducing an exposure light intensity or transmittance down to an object to be exposed and throughput.

The far UV light, such as excimer laser with a wavelength of 250 nm or less, particularly, ArF excimer laser having an oscillation wavelength of about 193 nm includes multiple oxygen absorption bands in this wavelength region. For example, as shown in FIG. 10, inert gas supplied from a plant facility 1100 is supplied to a tube port 1210 in an exposure apparatus 1200 to purge its optical system and reduce oxygen concentration in the exposure light path to a very low level for exposure light with a less absorbent and purified oscillation wavelength. Here, FIG. 10 is a schematic block diagram of a conventional exposure apparatus.

It is also known that the $F_2$ excimer laser with an oscillation wavelength of about 157 nm includes consecutive oxygen absorption bands in this wavelength region, and does not allow exposure light with a less absorbent wavelength to be selected like the ArF excimer laser. The vacuum UV light with a wavelength of about 157 nm includes continuous steam absorption bands that cannot be observed around 193 nm. The vacuum UV light with 157 nm is easily absorbed by ammonia ($NH_3$), carbon dioxide ($CO_2$), organic gases, etc., and a light absorption in the exposure light path increases substantially, which is not a problem for the vacuum UV light with a wavelength of 160 nm or less.

A fluctuant concentration of a light absorbent material in the exposure light path during exposure would result in an error or discord of the actual exposure dose relative to the target exposure dose, and deteriorate the above throughput and an exposure-dose control precision.

Accordingly, the impurity concentration should be monitored in gas constituents in the exposure light path in a projection exposure apparatus that uses the far UV light or excimer laser for controls over optical systems in their product adhesion, efficiency and the exposure dose.

However, the conventional exposure apparatus shown in FIG. 10 cannot detect the impurity concentration of the supplied gas, and might cause the projection exposure apparatus to accept the inert gas, etc. with an impermissible impurity concentration due to malfunctions etc. of the plant facility. The inert gas, etc., with an impermissible impurity concentration supplied to the exposure apparatus would cause the following disadvantages:

(1) The light absorption increases in the exposure light path and considerably lowers the throughput of the apparatus. (2) The fluctuant light absorption in the exposure light path during an exposure operation causes a change or error in the actual exposure dose to the target exposure dose, and deteriorates the exposure-dose control accuracy. (3) Impurities in the inert gas, etc. in the exposure light path photochemically react and cause resultant products to adhere to an optical element, such as a lens and a mirror in an optical system. The products lower performance, such as the optical efficiency, and might require an exchange for an expensive optical element depending on adhesions. (4) The impurities adhere to a pipeline system for guiding the inert gas, etc. to the exposure light path, and might require its cleansing or exchange.

BRIEF SUMMARY OF THE INVENTION

Accordingly, it is an exemplary object of the present invention to provide a gas supply unit and method, and an exposure system having the same, which detect the inert gas with an impurity concentration beyond a permissible value, and prevent the inert gas from entering the exposure apparatus.

A gas supply unit of one aspect according to the present invention supplies gas to a certain space via a channel, and includes a first switch mechanism located in the channel for selectively changing the channel of the gas.

The gas supply unit may further include a first detector, provided in the channel, for detecting an impurity concentration in the gas, wherein the first switch mechanism is located downstream in the channel from the first detector in a direction supplying the gas, the first switch mechanism switching the channel of the gas when the first detector detects an impermissible impurity concentration.

The first switch mechanism switches the channel to a predetermined channel that has a filter for removing the impurity. The first switch mechanism may switch the channel to a predetermined channel connected to a reserve gas container that contains gas with a permissible impurity concentration. The gas supply unit may further include a first delay part, located between the first detector and the first changing mechanism, for delaying a flow of the gas.

The gas supply unit may further include a second detector for detecting an impurity concentration of the gas that has passed through the filter, and a shut-off valve, provided between the second detector and the certain space, which shuts off the gas, the shut-off valve shutting off the gas when the second detector detects that the impermissible impurity concentration. The gas supply unit may further includes a second switch mechanism, located downstream from the shut-off valve in a direction supplying the gas in the channel, for switching the channel, the switch mechanism selecting another channel that is connected to a unit for supplying the gas with a permissible impurity concentration, the second switch mechanism switching the channel to the different channel via when the shut-off valve shuts off the channel.

The gas supply unit may further include a controller for controlling operations of the first or second switch mechanism based on a detection result of the first or second detector. The impurity may include one or more of ammonia, carbon oxide, organic substances, inorganic substances, oxygen, and water. The gas supply unit may further include a second delay part, located between the second detector and the shut-off valve, for delaying a flow of the gas. The first or second delay part may be a delay tube or a tank. The gas supply unit may further include an exhaust part, located between the shut-off valve and the certain space, for exhausting the gas. The gas supply unit may further include an alarm that notifies of the impermissible impurity concentration of the gas. The gas supply unit may further include a power supply of uninterruptible power.

A gas supply method of another aspect of the present invention that detects an impurity concentration of a gas in a certain space, and switches a gas supply channel such that the certain space has a permissible impurity concentration of the gas includes the steps of storing information on a permissible value, comparing the permissible value stored in the storing step with a detected impurity concentration, and switching the supply channel based on a result of the comparing step. The gas supply method may include the step of stopping supplying the gas to the supply channel based on the result of the comparing step.

"An exposure system of still another aspect includes the above gas supply unit, and an exposure apparatus that exposes an object by using ultraviolet light, for ultraviolet light and vacuum ultraviolet light as exposure light, and the channel filled with the gas supplied by the gas supply unit."

A device fabrication method of still another aspect of the present invention includes the steps of exposing an object using the above exposure system, and performing a predetermined process for the projected and exposed object. Claims for a device fabrication method for performing operations similar to that of the above exposure apparatus cover devices as intermediate and final products. Such devices include semiconductor chips like an LSI and VLSI, CCDs, LCDs, magnetic sensors, thin film magnetic heads, and the like.

Other objects and further features of the present invention will become readily apparent from the following description of the preferred embodiments with reference to accompanying drawings.

DETAILED DESCRIPTION OF THE PREFERRED EMBODIMENTS

Figure 1:
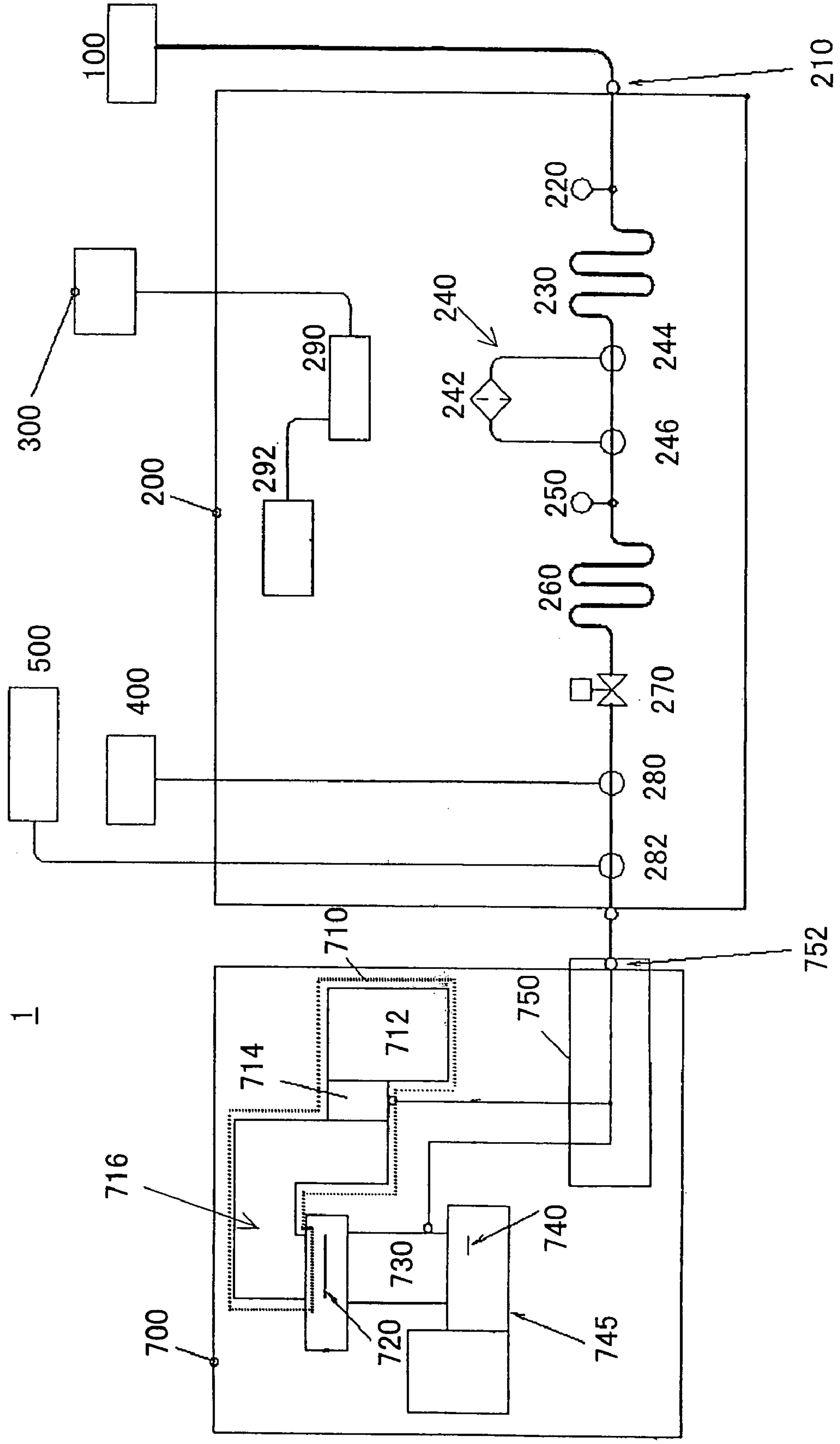
FIG. 1 is a schematic block diagram of an exposure system of a first embodiment according to the present invention.

A description will now be given of an exposure system as one embodiment according to the present invention with reference to accompanying drawings. However, the present invention is not limited to this embodiment, but each element may be replaced with an alternative element within the spirit and scope of the present invention. Here, FIG. 1 is a schematic block diagram of an exposure system 1 as a first embodiment of the present invention. As shown in FIG. 1, the exposure system 1 includes a plant facility 100, a gas supply unit 200, a power supply 300, an exhaust facility 400, a spare gas supply unit 500, and an exposure apparatus 700. The exposure system 1 of the present embodiment is a system that supplies the exposure apparatus 700 with inert gas for exposure with an impurity concentration equal to or less than a permissible value from the plant facility 100 via the gas supply unit 200.

Although the instant embodiment describes as if the gas supply unit, the spare gas supply unit, the exhaust facility, etc. are separate members from the exposure apparatus and the exposure system has all of them, the exposure apparatus may include the gas supply unit, the spare gas supply unit, the exhaust facility, etc. However, the factory facility 100 (for supplying inert gas and clean gas) is preferably a separate member from the exposure apparatus.

The plant facility 100 produces gas supplied to the exposure apparatus 700 via the gas supply unit 200. The gas produced by the plant facility 100 is inert gas or clean dry air with a permissible concentration of impurities including ammonia ($NH_3$), carbon dioxide ($CO_2$), organic and inorganic matters, oxygen ($O_2$), and water ($H_2O$). The instant embodiment separately forms the plant facility 100 that produces the inert gas and the gas supply unit 200, but they may be integrated into one body so as to serve as the gas supply unit 200, which will be described later.

The gas supply unit 200 detects an impurity concentration of gas produced from the plant facility 100 and supplies the exposure system 700 with the inert gas with a permissible impurity concentration. The gas supply unit 200 includes a port 210, a first detector 220, a delay tube 230, a channel 240, a second detector 250, a delay tube 260, a shut-off valve 270, valves 280 and 282, a controller 290 and an alarm 292. Preferably, the delay tubes 230 and 260 at least partially have an S shape.

The port 210 is connected to the plant facility 100, and separates the plant facility 100 and the gas supply unit 200 from each other. The port 210 introduces the inert gas produced by the plant facility 100 to the gas supply unit 200.

The first detector 220 detects the concentration of one or more of ammonia, carbon dioxide, organic and inorganic substances, oxygen, and water as impurities contained in the inert gas introduced from the port 210. The first detector 220 feeds a detected impurity-concentration result of the inert gas to the controller 290. The first detector 220 may use a dry ammonia analyzer, a zirconia oxygen densitometer, a thin-film aluminum oxide moisture meter, etc.

The delay tube 230 is arranged between the first detector 220 and the channel 240, which will be described later. The delay tube 230 is a first delay member that delays a flow of the inert gas with an impermissible impurity concentration (hereinafter called "contaminated inert gas") until a supply channel for the inert gas is switched to the channel 240 so that the contaminated inert gas may not enter the exposure apparatus 700.

The channel 240 includes a filter 242, and valves 244 and 246, and serves to remove the impurities of the contaminated gas. More specifically, when the first detector 220 detects that the gas supplied to the gas supply unit 200 from the plant facility 100 is the contaminated inert gas, the valve 244 switches the supply channel for the contaminated inert gas to the channel 240 and the filter 242 removes the impurity. The filter 242 may use a chemisorption refiner, and a porous substance, such as activated carbon and zeolite. The inert gas whose impurities are removed by the filter 242 returns to the original supply channel, and enters the second detector 250. The controller 290, which will be described later, switches the supply channel for the inert gas.

The second detector 250 detects a concentration of impurities, e.g., one or more of ammonia, carbon dioxide, organic and inorganic substances, oxygen, and water contained in the inert gas which have been removed by the filter 242 located in the channel 240. The second detector 250 determines whether the filter 242 has removed the impurity of the contaminated inert gas and whether the impurity concentration becomes permissible. The second detector 250 feeds an impurity concentration result of the inert gas to the controller 290. The controller 290 includes a microprocessor etc., determines whether the impurity concentration sent from the first and second detectors 220 and 250 is permissible or equal to or less than a predetermined value, and switches the valves if it is impermissible.

The delay tube 260 is arranged between the second detector 250 and the shut-off valve 270, which will be described later. The delay tube 260 is a second delay member that delays a flow of the inert gas that has passed through the filter 242 located in the channel 240 and its impurity concentration exceeds the permissible value, or when the filter 242 does not remove impurity sufficiently until the shut-off valve 270 works to prevent the contaminated gas from entering the exposure apparatus 700.

The shut-off valve 270 stops supplying the inert gas to the exposure apparatus 700 when the second detector 250 detects that the inert gas having passed through the channel 240 is contaminated.

The valve 280 switches channels for flowing cleansing gas to the exhaust the facility 400 when the impurity adheres to the pipeline system in the gas supply unit 200, and the pipeline system needs to be cleaned.

The valve 282 switches connections so that the inert gas may be supplied to the exposure apparatus 700 from the spare gas supply unit 500 to allow the exposure apparatus 700 to continue actions while the impurity that sticks to the tube in the gas supply unit 200 is cleansed from the tube.

The controller 290 is connected to and controls the first detector 220, the second detector 250, the valves 244, 246, 280, and 282, and the shut-off 270 in the gas supply unit 200. The controller 290 receives the impurity concentrations of the inert gas detected by the first and second detectors 220 and 250, compares them with the permissible value, and, controls switching actions of the valves 244, 246, 280 and 282, and the shut-off valve 270 based on these comparison results. The controller 290 has stored a permissible impurity-concentration value of the inert gas as a threshold in advance. A detailed description of its operations will be given later.

The alarm 292 informs via sounds, light, displays, etc. that the first and second detectors 220 and/or 250 have detected an impermissible impurity concentration of the inert gas. The alarm 292 can also inform of an operational status, such as cleaning and pipeline cleansing of the current gas supply unit 200, and identify a supply channel for the inert gas.

The power supply 300 supplies all parts of the gas supply unit 200 with power. The power supply 300 is an uninterruptible one for privately generating electric power to prevent the gas supply unit 200 from stopping its actions due to a power failure, etc. during actions of the exposure system 1 and the contaminated inert gas from entering the exposure apparatus 700 by mistake.

The exhaust facility 400 exhausts cleansing gas via the valve 280 when the impurity adheres to the tube of the gas supply unit 200, and the tube needs to be cleaned.

The spare gas supply unit (gas container) 500 supplies the exposure apparatus 700 with inert gas via the valve 282 in order to allow the exposure apparatus 700 to continue its actions even when the impurity has adhered to the tube and tube is being cleansed. The spare gas supply unit 500 may be of the same structure as that of the gas supply unit 200, or it may be a unit that supplies the inert gas whose purity is assured in advance.

Figure 2:
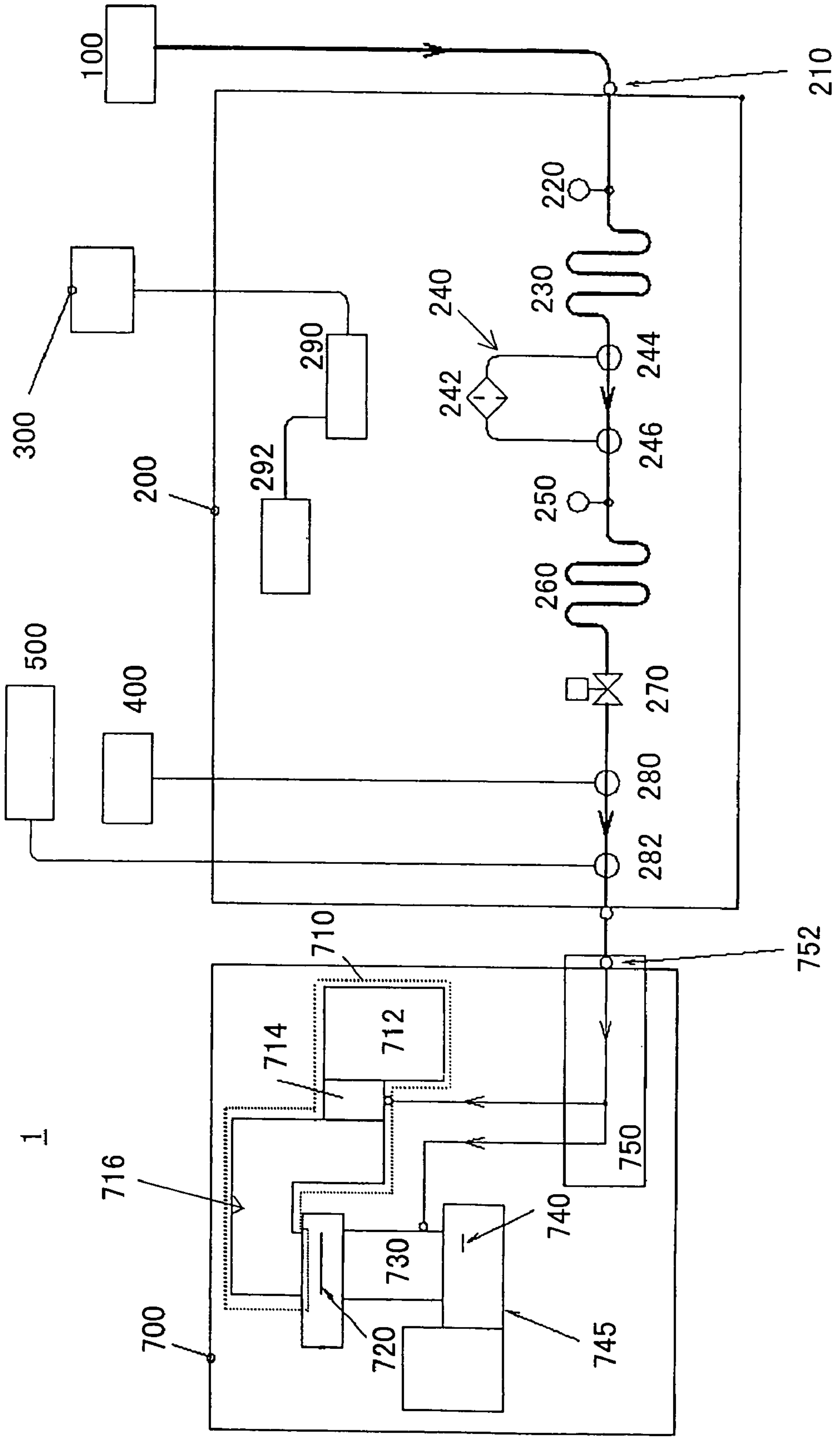
FIG. 2 is a view showing an inert-gas flow introduced into the gas supply unit shown in FIG. 1 with a permissible inert-gas impurity concentration.

Referring to FIGS. 2-5, a description will be given of the gas supply unit 200's operation and a flow of inert gas that fills the exposure light path in the exposure apparatus 700. Here, FIG. 2 is a view showing a flow of inert gas with a permissible impurity concentration, which has been introduced from the plant facility 100 to the gas supply unit 200 in a normal state. As illustrated, the flow of the inert gas is shown by an arrow.

Referring to FIG. 2, the inert gas produced by the plant facility 100 is initially introduced to the port 210 of the gas supply unit 200. The inert gas introduced to the port 210 enters the first detector 220, which in turn detects its impurity concentration. The concentration detected by the first detector 220 is sent to the controller 290, and compared with the permissible value. When the controller 290 determines that the inert gas has a permissible impurity concentration, it opens the valves 244 and 246, the shut-off valve 270, and the valves 280 and 282. The delay tube 230 then delays a flow of the inert gas. Then, the inert gas is supplied to the exposure apparatus 700 through the valve 244, the valve 246, the second detector 250, the delay tube 260, the shut-off valve 270, the valve 280, and the valve 282.

The second detector 250 in the present embodiment does not work since the inert gas has a permissible impurity concentration, but it may work when the impurity is likely to be mixed into the supply channel from the first detector 220 to the second detector 250. In this case, the impurity concentration of the inert gas is sent to the controller 290, which in turn closes the shut-off valve 270 to stop supplying the inert gas to the exposure apparatus 700 when determining that it exceeds the permissible value.

Figure 3:
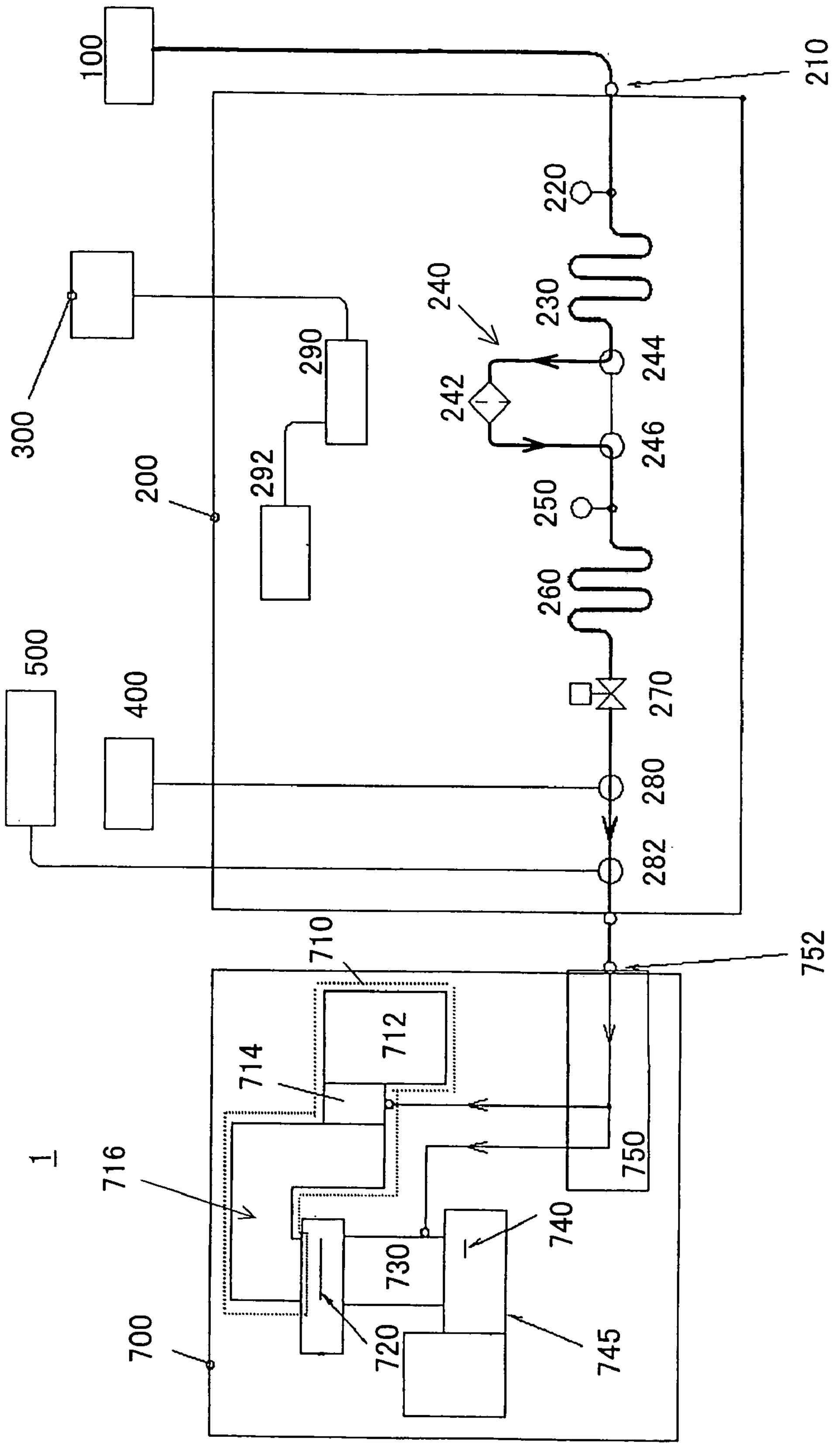
FIG. 3 is a view showing an inert-gas flow introduced into the gas supply unit shown in FIG. 1 with an impermissible inert-gas impurity concentration.

FIG. 3 is a view showing an inert-gas flow introduced from the plant facility 100 to the gas supply unit 220 when its impurity concentration exceeds the permissible value in an abnormal state. As illustrated, the flow of the inert gas is shown by an arrow.

Referring to FIG. 3, at first, the inert gas produced by the plant facility 100 is introduced to the port 210 of the gas supply unit 200. The inert gas introduced to the port 210 enters the first detector 220, which in turn detects its impurity concentration. The concentration detected by the first detector 220 is sent to the controller 290, and compared with the permissible value. When the controller 290 determines that the impurity concentration of the inert gas exceeds the permissible value, it switches the valves 244 and 246 to supply the contaminated inert gas to the channel 240, and prevent the contaminated inert gas from flowing downstream. The controller 290 uses the alarm 292 to notify an operator via sounds, light, displays, etc., that the inert gas has an impermissible impurity concentration, and switches the valves 244 and 246. The delay tube 230 delays a flow of the inert gas during this period, and the contaminated inert gas never enters the second detector 250 through the valves 244 and 246. The filter 242 removes the impurity from the contaminated inert gas in the channel 240. The inert gas whose impurity has been removed by the filter 242 enters the second detector 250 via the valve 246, which in turn detects a concentration of its impurities. The impurity concentration detected by the second detector 250 is sent the controller 290, and compared with the permissible value. When the controller 290 determines that the inert gas has a permissible impurity concentration, it opens the shut-off valve 270 and the valves 280 and 282. The delay tube 260 delays a flow of the inert gas during this period. The inert gas is then supplied to the exposure apparatus 700 through the shut-off valve 270 and the valves 280 and 282.

Figure 4:
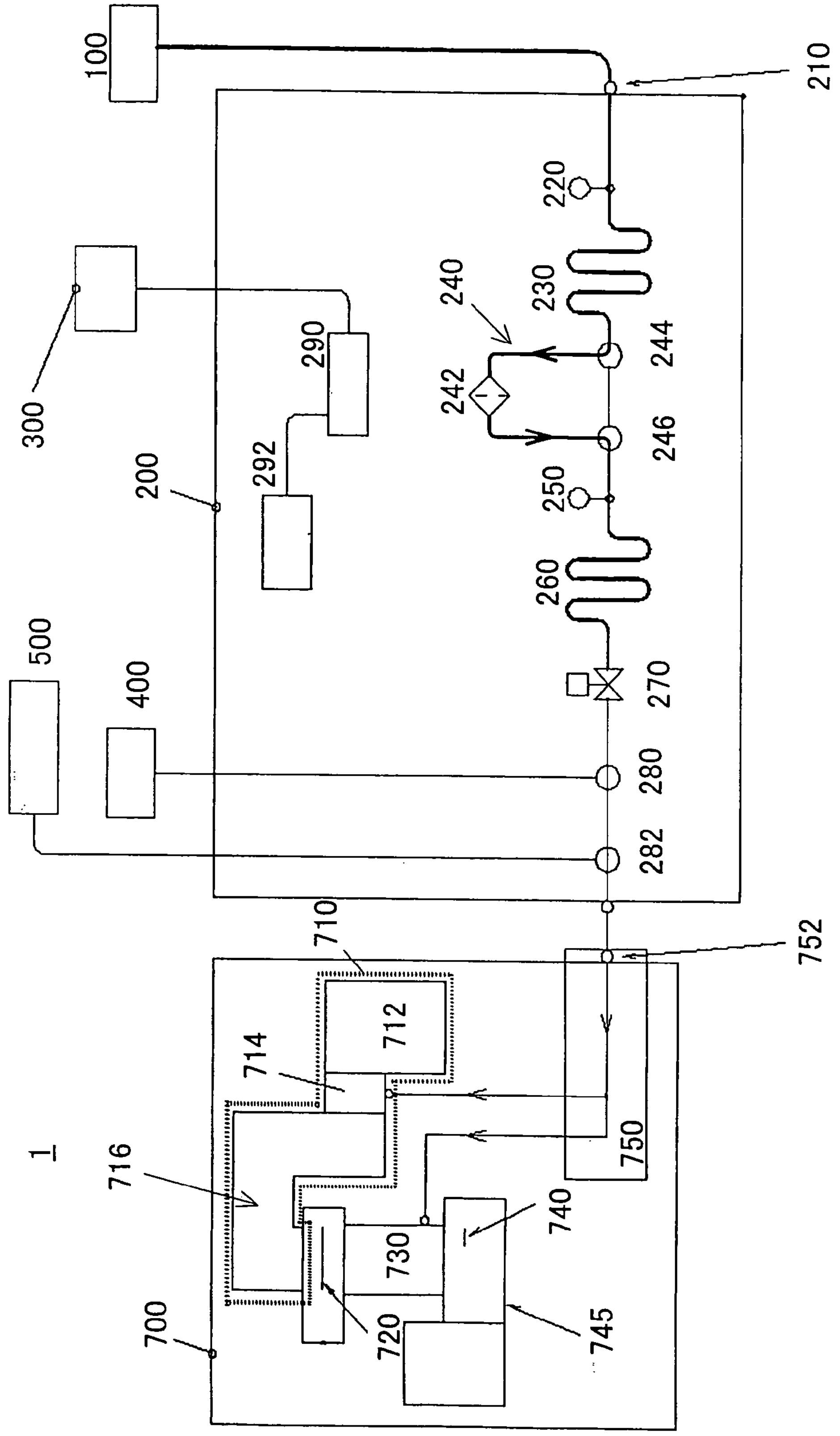
FIG. 4 is a view showing an inert-gas flow with impermissible impurity concentration that passes through a filter shown in FIG. 1.

When the controller 290 determines that the inert gas that has passed through the filter 242 of the channel 240 has an impermissible impurity concentration, it closes the shut-off valve 270 and stops supplying the inert gas to the exposure apparatus 700, as shown in FIG. 4. The controller 290 uses the alarm 292 to notify an operator via sounds, light, displays, etc. that the inert gas has an impermissible impurity concentration, as well as switching the valves 244 and 246. The delay tube 260 delays a flow of the inert gas this time, and the contaminated inert gas never enters the exposure apparatus 700 through the valves 280 and 282. Here, FIG. 4 is a view showing an inert-gas flow with impermissible impurity concentration in an abnormal state that passes through the filter 250 in the channel 240. As illustrated, the flow of the inert gas is shown by an arrow.

Figure 5:
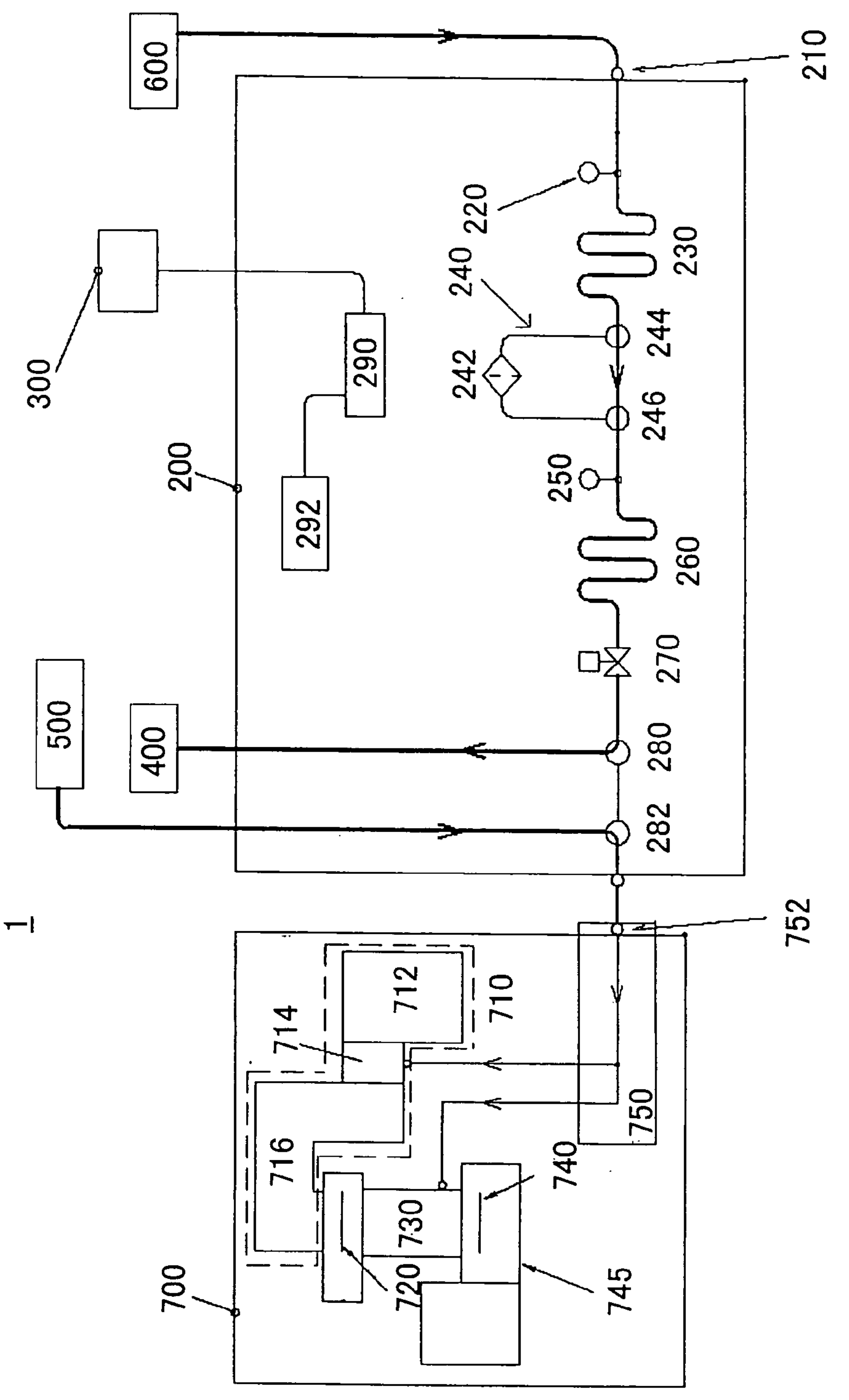
FIG. 5 is a view showing cleansing-gas and inert-gas flows when impurities are cleansed from the pipeline in the gas supply unit shown in FIG. 1.

FIG. 5 is a view showing cleansing-gas and inert-gas flows when the impurity is cleansed from the pipeline in the gas supply unit 200 when the impurity concentration of the inert gas introduced from the plant facility 100 to the gas supply unit 200 exceeds the permissible value. As illustrated, the flow of the cleansing gas and inert gas is shown by an arrow.

A cleansing gas supply unit 600 introduces a cleansing gas to the gas supply unit 200 via the port 210. The cleansing gas removes the impurity adhering to the pipeline system in the gas supply unit 200. The cleansing gas uses inert gas of nitrogen, etc. with a confirmedly permissible impurity concentration. Referring to FIG. 5, the valve 282 is switched such that inert gas is supplied to the exposure apparatus 700 from the spare gas supply unit 500 that has the inert gas with a confirmedly permissible impurity concentration. Thus, the exposure apparatus 700 may act even when the pipeline of the gas supply unit 200 is being cleaned. The port 210 is disconnected between the plant facility 100 and the gas supply unit 200, and connected to the cleansing gas supply unit 600. Then, the valve 280 is switched to connect the flow channel for the cleansing gas to the exhaust facility 400.

The cleansing gas is introduced from the cleansing gas supply unit 600 to the port 210 in the gas supply unit 200. The cleansing gas introduced to the port 210 is exhausted to the exhaust facility 400 through the first detector 220, the delay tube 230, the valves 244 and 246, the second detector 250, the delay tube 260, the shut-off valve 270 and the valve 280. The cleansing gas then removes the impurity that clings to the pipeline in the gas supply unit 200.

Upon completion of removal of the impurity adhering to the pipeline in the gas supply unit 200, the port 210 is disconnected from the cleansing gas supply unit 600 and connected to the plant facility 100, which has the inert gas with a confirmedly permissible impurity concentration. The inert gas is introduced from the plant facility 100 to the gas supply unit 200, and exhausted from the exhaust facility 400. The first and second detectors 220 and 250 detect the impurity concentration of the inert gas. The concentrations detected by the first and second detectors 220 and 250 are sent to the controller 290 for comparison with the permissible value. When the inert gas has a confirmedly permissible impurity concentration, the valves 280 and 282 are switched such that the inert gas from the plant facility 100 is supplied to the exposure apparatus 700. When the impurity concentration of the inert gas exceeds the permissible value, the plant facility 100 and the port 210 are disconnected, and instead, the cleansing gas supply unit 600 is connected to repeat the cleaning of the gas supply unit 200's pipeline by using the cleansing gas.

Figure 6:
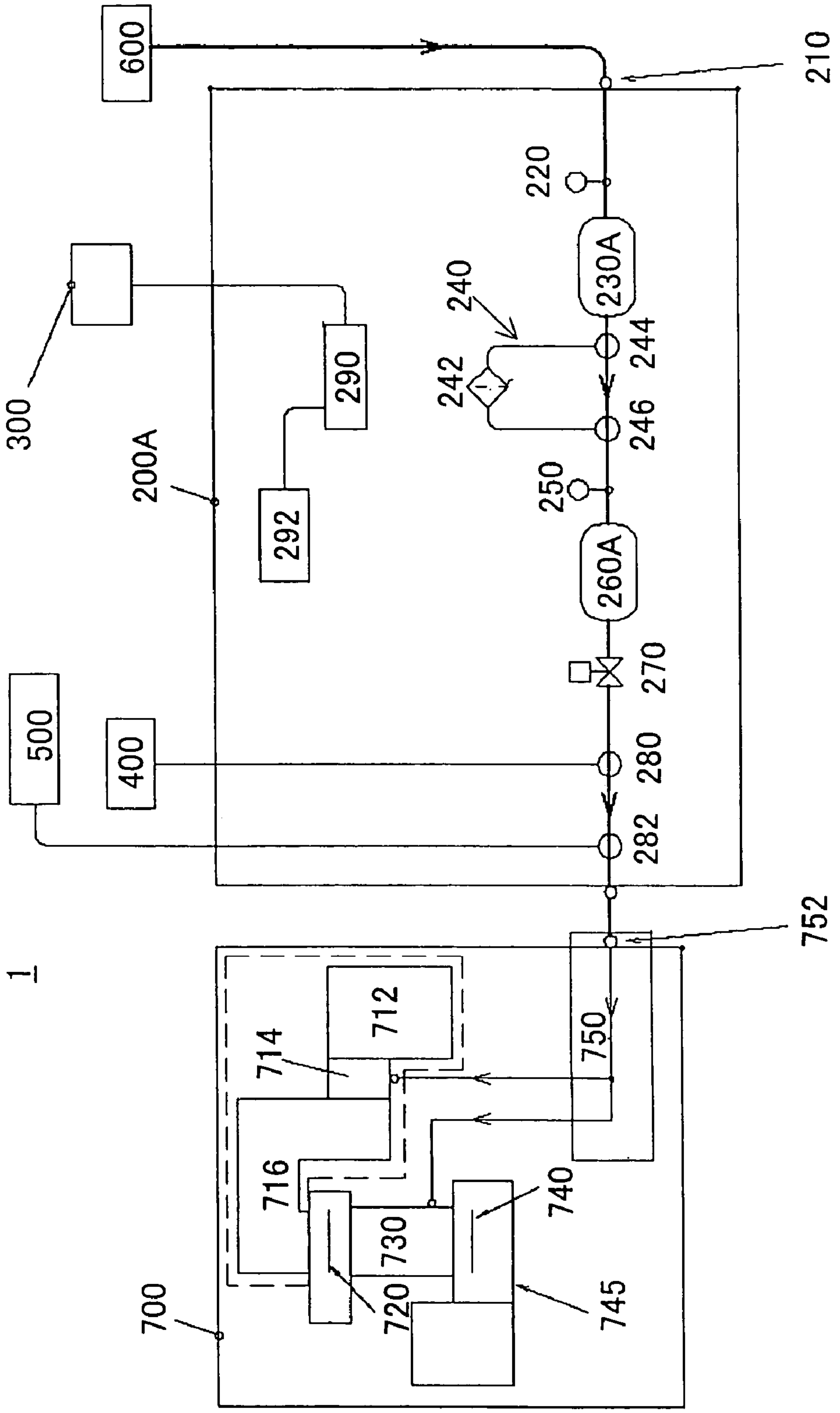
FIG. 6 is a schematic block diagram of a gas supply unit as a variation of the gas supply unit shown in FIG. 1.

Referring now to FIG. 6, a description will be given of a gas supply unit 200A as a variation of the gas supply unit 200. The gas supply unit 200A differs from the gas supply unit 200 in the delay tubes 230 and 260 as the first and second delay parts. Here, FIG. 6 is a schematic block diagram of a gas supply unit 200A as a variation of the gas supply unit 200 shown in FIG. 1.

Similar to the gas supply 200, the gas supply unit 200A detects an impurity concentration of the inert gas produced by the plant facility 100 and supplies to the exposure apparatus 700 the inert gas with a permissible impurity concentration.

A delay tank 230A is arranged between the first detector 220 and the channel 240, and serves as a first delay member that delays a flow of the inert gas with an impermissible impurity concentration until the supply channel for the inert gas is switched to the channel 240 so that the contaminated inert gas may not enter the exposure apparatus 700.

A delay tank 260A is arranged between the second detector 250 and the shut-off valve 270, and serves as a second delay member that delays a flow of the inert gas that has passed through the filter 242 of the channel 240 and includes an impermissible impurity concentration or when the filter 242 does not remove the impurity sufficiently until the shut-off valve 270 works, so that the contaminated inert gas may not enter the exposure apparatus 700.

The gas supply unit 200A's action and the flow of the inert gas filling the exposure light path in the exposure apparatus 700 are the same as those of the gas supply unit 200, and a description thereof will be omitted.

Turning back to FIG. 1 again, the exposure apparatus 700 includes an illumination apparatus 710 that illuminates a mask or reticle (these terms are used interchangeably in the present application) 720 which forms a pattern, a stage 745 that supports a plate, and a projection optical system 730 that projects diffracted light arising from the illuminated mask pattern to the plate 740, and a piping unit 750.

The exposure apparatus 700 is a projection exposure apparatus that exposes a circuit pattern formed on the mask 720 onto the plate 740, e.g., in a step-and-repeat or step-and-scan manner. Such an exposure apparatus is suitable for a photolithography process of a sub-micron or a quarter-micron or less. A description will be given below of a step-and-scan exposure apparatus (which is also referred to as a "scanner") as an example. The "step-and-scan" manner, as used herein, is one mode of exposure method which exposes a pattern on a mask onto a wafer by continuously scanning the wafer relative to the mask, and by moving, after a shot of exposure, the wafer stepwise to the next exposure area to be shot. The "step-and-repeat" manner is another mode of exposure method which moves a wafer stepwise to an exposure area for the next shot every shot onto the wafer.

The illumination apparatus 710 illuminates the mask 720 which forms a circuit pattern to be transferred, and includes a light source section 712, a delivery optics unit 714, and an illumination optical system 716.

The light source section 712 employs, e.g., laser as a light source. The laser may use ArF excimer laser with a wavelength of approximately about 193 nm, KrF excimer laser with a wavelength of about 248 nm, $F_2$ excimer laser with a wavelength of about 153 nm, etc. However, a kind of laser is not limited to excimer laser. For example, YAG laser can be used, and the number of laser units is not limited. For example, if two units of solid laser that operates independently are used, no coherence between these solid laser units exists, and thus, speckles arising from the coherence will be reduced considerably. In order to reduce speckles, it would be preferable to oscillate an optical system in a straight or rotating manner. When the light source section 712 uses laser, it is desirable to employ a beam shaping optical system that shapes a parallel beam from a laser source to a desired beam shape, and an incoherently turning optical system that turns a coherent laser beam into an incoherent one. A light source applicable to the light source part 712 is not limited to the laser, but may use one or more lamps such as a mercury lamp, xenon lamp, etc.

The delivery optics unit 714 guides light from the light source section 712 to the illumination optical system 716. The illumination optical system 716 is an optical system that illuminates the mask 729, including a lens, a mirror, a light integrator, a stop, and the like, for example, in the order of a condenser lens, a fly-eye lens, an aperture stop, a condenser lens, a slit, and an imaging optical system. The illumination optical system 716 can use any light whether it is axial or non-axial light. The light integrator may include a fly-eye lens or an integrator formed by stacking two sets of cylindrical lens array plates (or lenticular lenses), and be replaced with an optical rod or a diffractive element.

The mask 720 forms a circuit pattern or an image to be transferred, and is made, for example, of quartz and supported and driven by a mask stage (not shown). Diffracted light through the mask 720 is projected onto the plate 740 through the projection optical system 730. The plate 740 is an object to be exposed such as a wafer or a liquid crystal plate, onto which resist is applied. The mask 720 and plate 740 are located in a conjugate relationship. When the exposure apparatus 700 is a scanner, it transfers a pattern on the mask 720 onto the plate 740 by scanning the mask 720 and plate 740. When the exposure apparatus 700 is a stepper (or a "step-and-repeat" exposure apparatus), it exposes while resting the mask 720 and plate 740.

The projection optical system 730 may use an optical system including plural lens elements, an optical system including plural lens elements and at least one concave mirror (a catadioptric optical system), an optical system including plural lens elements and at least one diffractive optical element such as a kinoform, a full mirror type optical system, and so on. Any necessary correction of the chromatic aberration may use plural lens units made from glass materials having different dispersion values (Abbe values), or arrange a diffractive optical element such that it disperses in a direction opposite to that of the lens unit.

Photoresist is applied onto the plate 740. A photoresist application step includes a pretreatment, an adhesion accelerator application treatment, a photo-resist application treatment, and a pre-bake treatment. The pretreatment includes cleaning, drying, etc. The adhesion accelerator application treatment is a surface reforming process so as to enhance the adhesion between the photo resist and a base (i.e., a process to increase the hydrophobicity by applying a surface active agent), through a coat or vaporous process using an organic film such as HMDS (Hexamethyl-disilazane). The pre-bake treatment is a baking (or burning) step, softer than that after development, which removes the solvent.

The stage 745 supports the plate 740. The stage 745 may use any structure known in the art, and thus a detailed description of its structure and operations is omitted. For example, the stage 745 may use a linear motor to move the plate 740 in directions X and Y. The mask 720 and plate 740 are, for example, scanned synchronously, and the positions of the stage 745 and mask stage (not shown) are monitored, for example, by a laser interferometer and the like, so that both are driven at a constant speed ratio. The stage 745 is installed on a stage stool supported on the floor and the like, for example, via a damper, and the mask stage and the projection optical system 730 are installed on a lens barrel stool (not shown) supported, for example, via a damper on a base-frame placed on the floor and the like.

The piping unit 750 has a pipeline port 752, and supplies the inert gas into the exposure light path while decompressing its pressure and adjusting its flow rate, the inert gas that is supplied with a permissible impurity concentration from the gas supply unit 200 connected via the pipeline port 752. The pipeline unit 750 allows the exposure light path to be filled with the inert gas with a permissible impurity concentration. This may prevent extremely lowered throughput due to augmented light absorption in the exposure light path caused by impurity of the inert gas, the degraded exposure-dose control accuracy due to the fluctuant light absorption in the exposure light path during exposure and fluctuant or erroneous exposure dose, and lowered performance such as optical efficiency as a result of adhesions of impurity onto an optical element, such as a lens and a mirror in an optical system and its photochemical reactions in the exposure light path and product generated by the reactions.

In exposure, light emitted from the light source section 712 uses the illumination optical system 716 to Koehler-illuminate the mask 720. Light passing the mask 720 and reflecting the mask pattern is imaged onto the plate 740 by the projection optical system 730. Since the inside of the exposure apparatus 700's exposure light path is filled with the inert gas supplied with a permissible impurity concentration by the inventive gas supply unit 200, UV, far UV light and vacuum UV light are transmitted with high transmittance, and may provide devices (such as semiconductor devices, LCD devices, image pick-up devices (such as CCDs), thin-film magnetic heads, etc. with high throughput and high economical efficiency.

Figure 7:
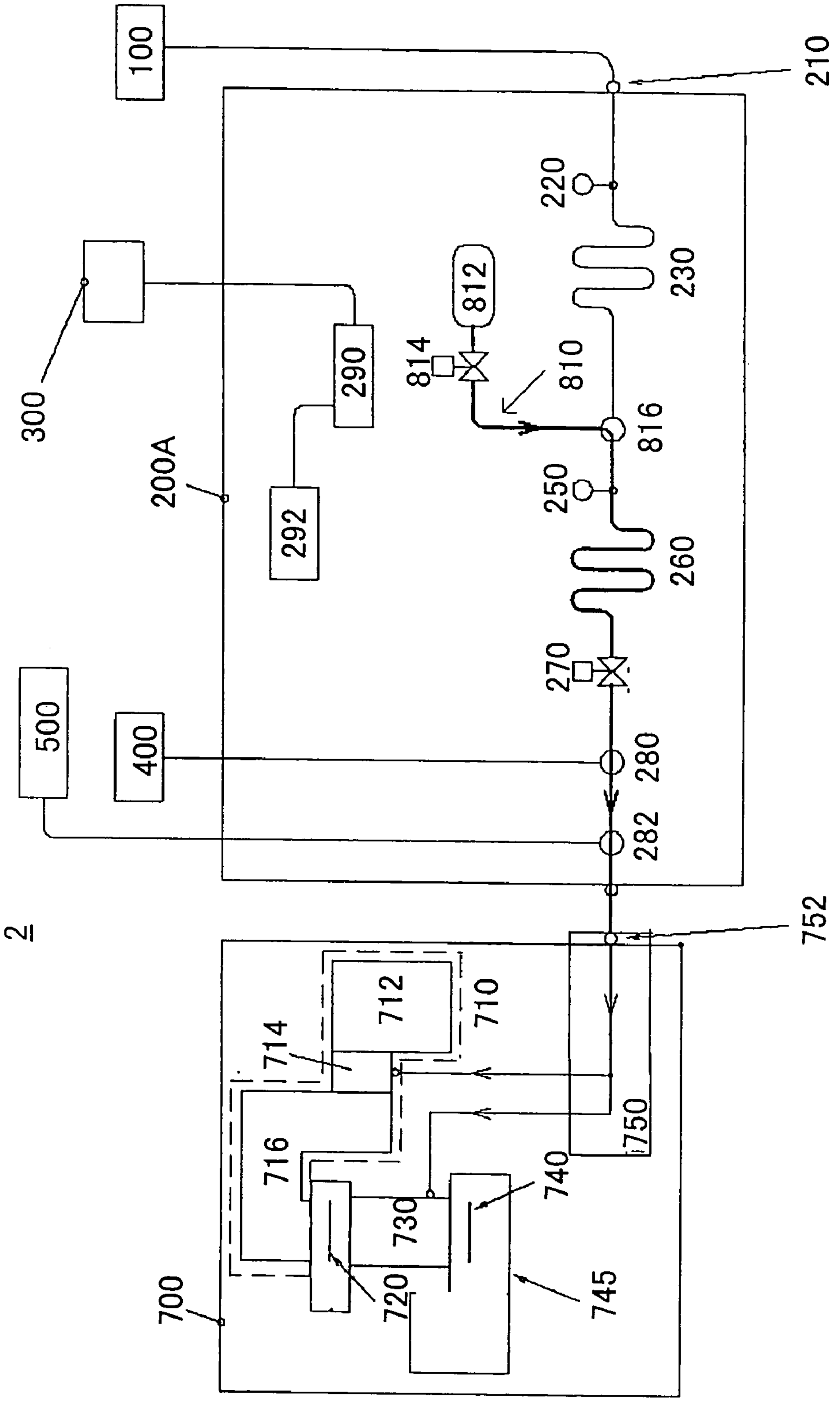
FIG. 7 is a schematic block diagram of an exposure system of a second embodiment according to the present invention.

Referring now to FIG. 7, a description will be given of an exposure system 2 of a second embodiment according to the present invention. FIG. 7 is a schematic block diagram of the exposure system 2 of the second embodiment according to the present invention. The exposure system 2 in FIG. 7 is similar to the exposure system 1 in FIG. 1, but differs in the structure of the gas supply unit 200. Incidentally, for the same elements as are shown in the exposure system 1 in FIG. 1, the same reference numerals are assigned such that a duplicate description of them is avoided.

As shown in FIG. 7, the exposure system 2 includes the plant facility 100, a gas supply unit 800, an electric power supply 300, the exhaust facility 400, the spare gas supply unit 500, and the exposure apparatus 700. The exposure system 2 of this embodiment is a system that uses the gas supply unit 800 to supply the exposure apparatus 700 with the inert gas with a permissible impurity concentration from the plant facility 100 for exposure.

The gas supply unit 800 supplies the exposure apparatus 700 with the inert gas with a permissible impurity concentration and detects the impurity concentration of the inert gas produced by the plant facility 100. As illustrated, the gas supply unit 800 has a gas container 812 in place of the filter 242 and the valves 244 and 246, the shut-off valve 814, and the valve 816 in the channel 810.

The channel 810 includes the gas container 812, the shut-off valve 814 and valve 816. The channel 810 is to provide the exposure apparatus 700 with the inert gas from the gas container 812 that is filled with the apparently purified inert gas, when the first detector 220 has detected that the inert gas supplied from the plant facility 100 to the gas supply unit 800 is contaminated inert gas. The shut-off valve 814 opens and closes the gas container 812. The valve 816 switches a supply channel of the inert gas to the channel 810. The controller 290 controls switching of the supply channel of the inert gas or the opening/closing of the shut-off valve 814 and the switching of the valve 816.

A description will be given of the operations of the gas supply unit 800 and a flow of the inert gas filling the exposure light path in the exposure apparatus 800. FIG. 7 indicates the flow of the inert gas by an arrow.

At first, the inert gas produced by the plant facility 100 is introduced to the port 210 of the gas supply unit 800. The inert gas introduced to the port 210 enters the first detector 220, which in turn detects its impurity concentration. The concentration detected by the first detector 220 is sent to the controller 290, and compared with the permissible value.

If the controller 290 determines that the inert gas has a permissible impurity concentration, it controls the valve 816 to switch the channel supplying the inert gas to the channel 810, and prevents the contaminated inert gas from flowing downstream. The controller 290 notifies an operator through sounds, light, displays, etc. of an impermissible impurity concentration of the inert gas via the alarm 292. The delay tube 230 delays a flow of the inert gas this time, and the contaminated inert gas never enters the valve 816 and the second detector 250. The controller 290 then opens the shut-off valve 814, which allows the inert gas to flow from the gas container 812 via the valve 816 into the second detector 250, which in turn detects the impurity concentration. The impurity concentration detected by the second detector 250 is sent to the controller 290, and compared with the permissible value. When the controller 290 determines that the inert gas has a permissible impurity concentration, it opens the shut-off valve 270, and the valves 280 and 282. The delay tube 260 delays a flow of the inert gas during this time. Then, the inert gas is supplied to the exposure apparatus 700 through the shut-off valve 270, and the valves 280 and 282.

When the controller 290 determines that the inert gas that is supplied from the gas container 812 in the channel 810 and has an impermissible impurity concentration, it closes the shut-off valve 270 and stops supplying the inert gas to the exposure apparatus 700. The controller 290 closes the shut-off valve 270 and notifies an operator through sounds, light, displays, etc. from the alarm 292 that the inert gas has an impermissible impurity concentration. The delay tube 260 delays a flow of the inert gas during this time, and the contaminated inert gas never enters the valves 280 and 282 and flows into the exposure 700.

Figure 8:
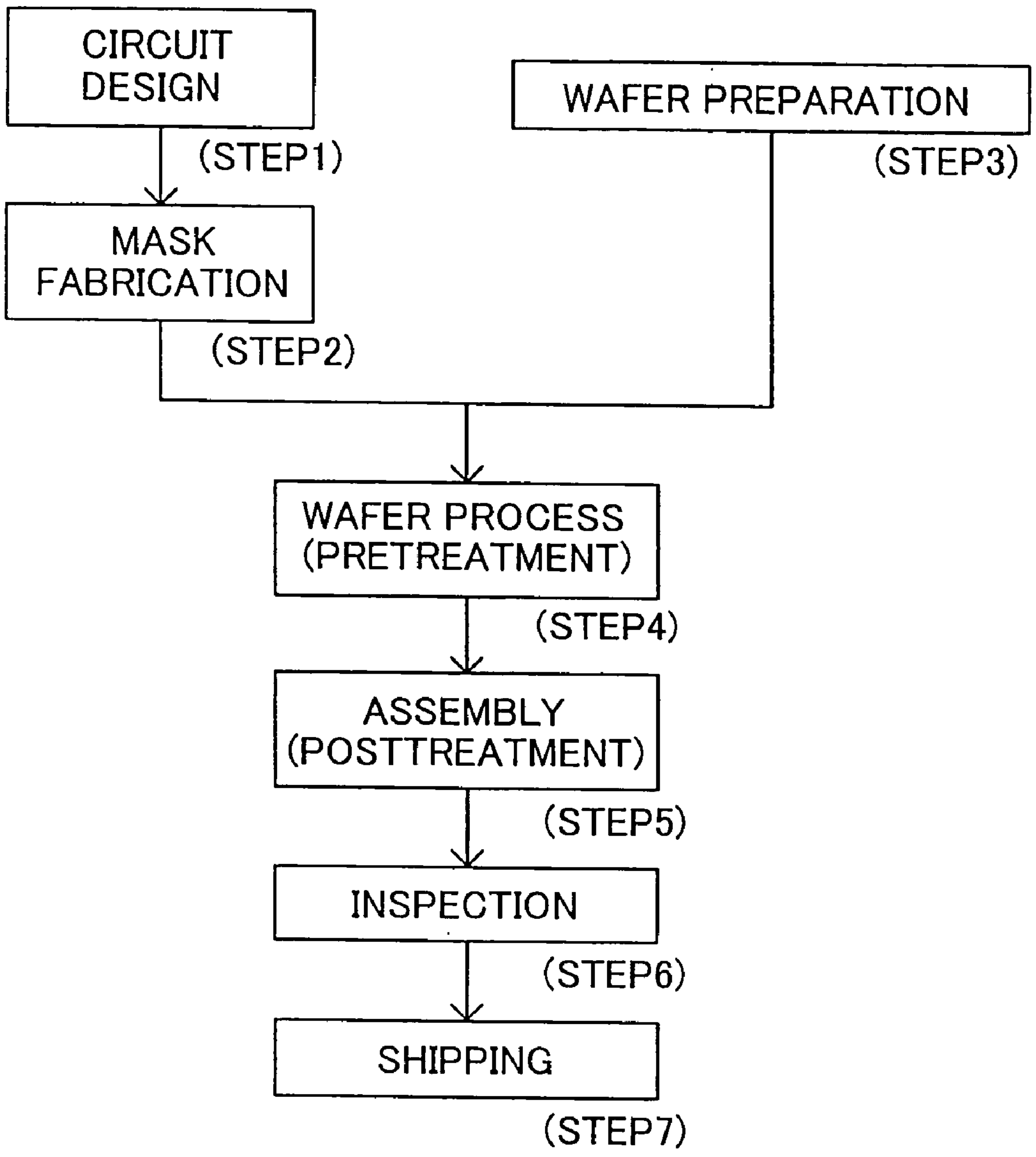
FIG. 8 is a flowchart for a device fabrication method including an inventive exposure system.
Figure 9:
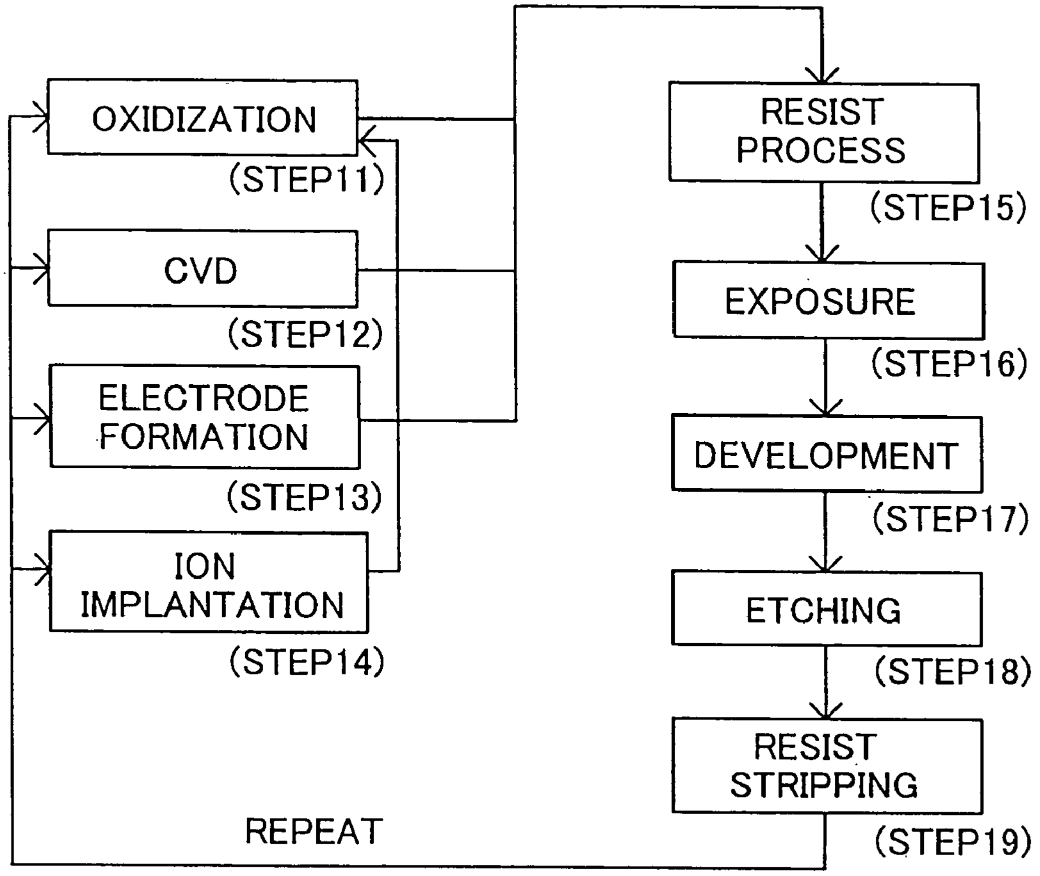
FIG. 9 is a flowchart for a wafer process shown in FIG. 8.
Figure 10:
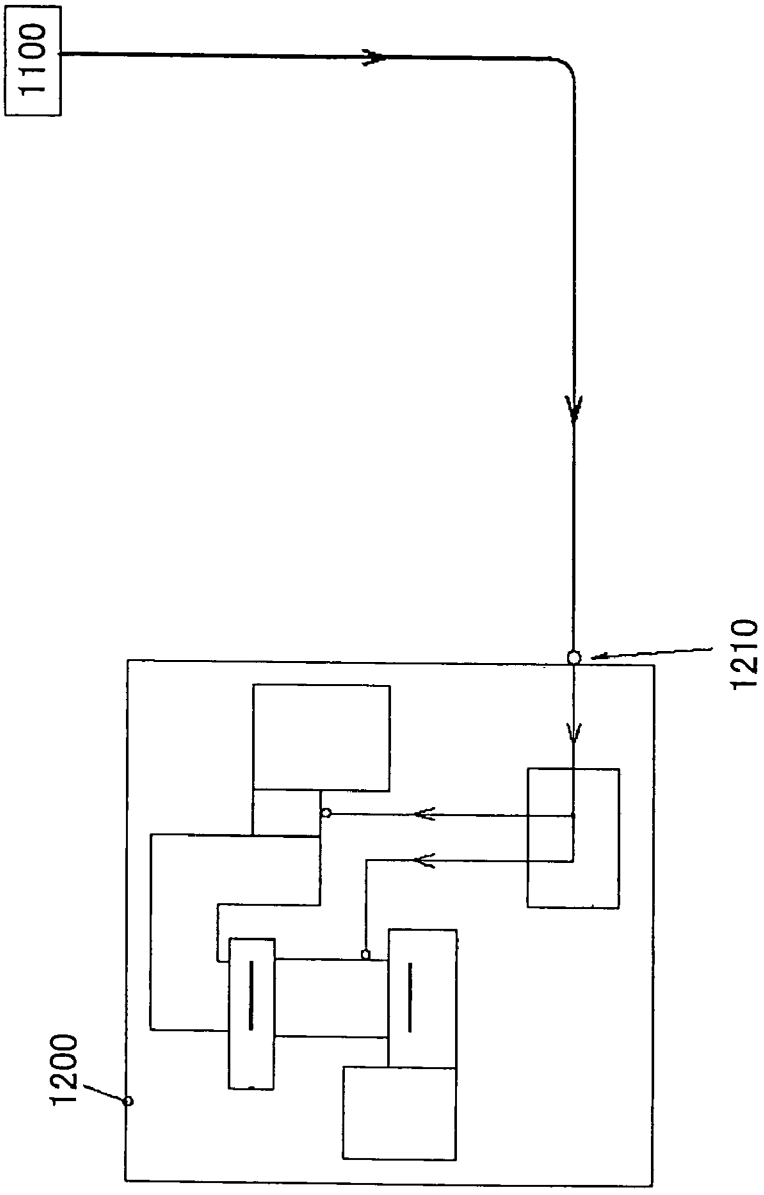
FIG. 10 is a schematic block diagram of a conventional exposure apparatus.

Referring now to FIGS. 8 and 9, a description will be given of an embodiment of a device fabricating method using the above exposure apparatus 1. FIG. 8 is a flowchart for explaining a fabrication of devices (i.e., semiconductor chips such as IC and LSI, LCDs, CCDs, etc.). Here, a description will be given of a fabrication of a semiconductor chip as an example. Step 1 (circuit design) designs a semiconductor device circuit. Step 2 (mask fabrication) forms a mask having a designed circuit pattern. Step 3 (wafer preparation) manufactures a wafer using materials such as silicon. Step 4 (wafer process), which is referred to as a pretreatment, forms actual circuitry on the wafer through photolithography using the mask and wafer. Step 5 (assembly), which is also referred to as a posttreatment, forms into a semiconductor chip the wafer formed in Step 4 and includes an assembly step (e.g., dicing, bonding), a packaging step (chip sealing), and the like. Step 6 (inspection) performs various tests for the semiconductor device made in Step 5, such as a validity test and a durability test. Through these steps, a semiconductor device is finished and shipped (Step 7).

FIG. 9 is a detailed flowchart of the wafer process in Step 4. Step 11 (oxidation) oxidizes the wafer's surface. Step 12 (CVD) forms an insulating film on the wafer's surface. Step 13 (electrode formation) forms electrodes on the wafer by vapor disposition and the like. Step 14 (ion implantation)

implants ion into the wafer. Step 15 (resist process) applies a photosensitive material onto the wafer. Step 16 (exposure) uses the exposure apparatus 200 to expose a circuit pattern on the mask onto the wafer. Step 17 (development) develops the exposed wafer. Step 18 (etching) etches parts other than a developed resist image. Step 19 (resist stripping) removes disused resist after etching. These steps are repeated, and multilayer circuit patterns are formed on the wafer. The device fabrication method of this embodiment may manufacture higher quality devices than the conventional one.

The above gas supply unit and method, and exposure systems may detect the inert gas with an impermissible impurity concentration, and prevent that inert gas from entering an exposure apparatus. This may prevent extremely lowered throughput due to augmented light absorption in the exposure light path caused by impurity of the inert gas, the degraded exposure-dose control accuracy due to the fluctuant light absorption in the exposure light path during exposure and fluctuant or erroneous exposure dose, and lowered performance such as optical efficiency as a result of adhesions of impurity onto an optical element, such as a lens and a mirror in an optical system and its photochemical reactions in the exposure light path and product generated by the reactions. This may also reduce cost incurred in exchanging optical elements and pipelines to which the impurities have adhered.

Only when an impurity concentration of supplied inert gas exceeds a permissible value, a filter removes the impurity or a gas container of the inert gas works with the purified inert gas. Thus, a regular exchange of the filter or gas container is unnecessary, restraining the running cost.

Further, the present invention is not limited to these preferred embodiments, and various variations and modifications may be made without departing from the scope of the present invention.

The gas supply unit, the supply method, and the exposure system of the instant invention can detect the inert gas with an impermissible impurity concentration, and prevent that inert gas from entering the exposure apparatus.

What is claimed is:

1. An exposure system comprising:

an exposure apparatus for exposing a wafer to ultraviolet light, said exposure apparatus including an optical system which has a path of the light; and a gas supply unit including a first channel connecting a plant facility and a first space including the path of the light without any intervening spaces including the path of the light and configured to supply gas from the plant facility to the first space, wherein said gas supply unit includes a first detector configured to detect an impurity concentration in said first channel, a second channel connected to said first channel downstream of said first detector, and a switch mechanism configured to switch said first and second channels based on the impurity concentration detected by said first detector.

2. A system according to claim 1, further comprising a filter provided in said second channel and configured to remove an impurity, said second channel being connected to the first space.

3. A system according to claim 1, further comprising a reserve gas container connected to said second channel and configured to contain gas with a permissible impurity concentration.

4. A system according to claim 1, further comprising a first delay part provided between said first detector and said switching mechanism and configured to delay a flow of gas.

5. A system according to claim 2, further comprising:

a second detector configured to detect an impurity concentration of gas that has passed through said filter; and a shut-off valve provided between said second detector and the first space and configured to shut off said second channel based on the impurity concentration detected by said second detector.

6. A system according to claim 5, further comprising another gas supply unit configured to supply gas, a third channel connecting said other gas supply unit and said second channel downstream of said shut-off valve, wherein said apparatus is configured so that said other gas supply unit supplies gas to the first space via said third channel based on the impurity concentration detected by said second detector.

7. A system according to claim 6, further comprising a valve configured to connect said third channel to said second channel, and a controller configured to control an operation of said valve based on the impurity concentration detected by said second detector.

8. A system according to claim 1, further comprising a controller configured to control an operation of said switch mechanism based on the impurity concentration detected by said first detector.

9. A system according to claim 5, further comprising a second delay part provided between said second detector and said shut-off valve and configured to delay a flow of gas.

10. A system according to claim 4, wherein said first delay part includes one of a tube and a tank.

11. A system according to claim 9, wherein said second delay part includes one of a tube and a tank.

12. A system according to claim 5, further comprising an exhaust part provided between said shut-off valve and the first space and configured to exhaust gas.

13. A system according to claim 1, further comprising an alarm configured to notify an impermissible impurity concentration detected by said first detector.

14. A system according to claim 1, further comprising an uninterruptible power supply configured to supply said gas supply unit with power.

15. A method of manufacturing a device, said method comprising steps of:

exposing a wafer to light using an exposure system as defined in claim 1;

developing the exposed wafer; and processing the developed wafer to manufacture the device.

* * * * *